(12) United States Patent
Sandhu et al.

(10) Patent No.: US 10,744,131 B2
(45) Date of Patent: Aug. 18, 2020

(54) ABUSE-RESISTANT DRUG FORMULATIONS

(71) Applicant: Kashiv BioSciences, LLC, Bridgewater, NJ (US)

(72) Inventors: Harpreet Kaur Sandhu, West Orange, NJ (US); Siva Ram Kiran Vaka, Piscataway, NJ (US); Ashish Chatterji, East Brunswick, NJ (US); Dipen Desai, Whippany, NJ (US); Wantanee Phuapradit, Montville, NJ (US); Navnit H. Shah, Clifton, NJ (US)

(73) Assignee: KASHIV BIOSCIENCES, LLC, Bridgewater, NJ (US)

( * ) Notice: Subject to any disclaimer, the term of this patent is extended or adjusted under 35 U.S.C. 154(b) by 205 days.

(21) Appl. No.: 15/108,157

(22) PCT Filed: Dec. 31, 2014

(86) PCT No.: PCT/US2014/072968
§ 371 (c)(1),
(2) Date: Jun. 24, 2016

(87) PCT Pub. No.: WO2015/103379
PCT Pub. Date: Jul. 9, 2015

(65) Prior Publication Data
US 2016/0317530 A1    Nov. 3, 2016

Related U.S. Application Data

(60) Provisional application No. 61/922,158, filed on Dec. 31, 2013.

(51) Int. Cl.
*A61K 31/485* (2006.01)
*A61K 47/14* (2017.01)
(Continued)

(52) U.S. Cl.
CPC ............ *A61K 31/485* (2013.01); *A61K 9/485* (2013.01); *A61K 9/4858* (2013.01);
(Continued)

(58) Field of Classification Search
CPC .... A61K 31/485; A61K 47/34; A61K 9/4866; A61K 9/4858; A61K 47/26;
(Continued)

(56) References Cited

U.S. PATENT DOCUMENTS 8,298,579 B2    10/2012  Abreu
2008/0206321 A1*  8/2008  Yum .................... A61K 9/4858
                                                                424/456

(Continued)

FOREIGN PATENT DOCUMENTS

EP   2067471 A1    6/2009
WO   2005009409 A2  2/2005
WO   2008150526 A1  12/2008

OTHER PUBLICATIONS

W Mullican et al: "Tramadol/acetaminophen combination tablets and codeine/acetaminophen combination capsules for the management of chronic pain: a comparative trial", Clinical Therapeutics, vol. 23, No. 9, Sep. 1, 2001 (Sep. 1, 2001), pp. 1429-1445, XP055168867.
(Continued)

*Primary Examiner* — Angela C Brown-Pettigrew
(74) *Attorney, Agent, or Firm* — Kashiv BioSciences, LLC; Vandana Awasthi

(57) ABSTRACT

Disclosed are abuse resistant oral pharmaceutical compositions that reduce the likelihood of improper administration of drugs that are susceptible to abuse. The oral pharmaceutical formulations contain abuse deterrent agents that cause discomfort to the user when administered in an improper manner and make the extraction of an active ingredient more
(Continued)

Release of drug from single unit capsule in water difficult. Methods of making and using the compositions are also disclosed.

20 Claims, 1 Drawing Sheet

(51) Int. Cl.
*A61K 47/20* (2006.01)
*A61K 47/44* (2017.01)
*A61K 47/34* (2017.01)
*A61K 9/48* (2006.01)
*A61K 47/26* (2006.01)
*A61K 31/135* (2006.01)
*A61K 31/167* (2006.01)
*A61K 47/02* (2006.01)
*A61K 47/10* (2017.01)
*A61K 47/18* (2017.01)
*A61K 47/22* (2006.01)

(52) U.S. Cl.
CPC .......... *A61K 9/4866* (2013.01); *A61K 9/4875* (2013.01); *A61K 31/135* (2013.01); *A61K 31/167* (2013.01); *A61K 47/02* (2013.01); *A61K 47/10* (2013.01); *A61K 47/14* (2013.01); *A61K 47/18* (2013.01); *A61K 47/20* (2013.01); *A61K 47/22* (2013.01); *A61K 47/26* (2013.01); *A61K 47/34* (2013.01); *A61K 47/44* (2013.01)

(58) Field of Classification Search
CPC ...... A61K 31/135; A61K 47/10; A61K 47/22; A61K 47/14; A61K 47/20; A61K 47/44
See application file for complete search history.

(56) References Cited

U.S. PATENT DOCUMENTS

2010/0260844 A1* 10/2010 Scicinski ............. A61K 9/1617
424/484
2014/0271593 A1 9/2014 Bromley
2014/0271835 A1* 9/2014 Wengner .................. A61K 9/10
424/452

OTHER PUBLICATIONS

International Search Report and Written Opinion for Application No. PCT/US2014/072968 dated Feb. 18, 2015.

* cited by examiner

Release of drug from single unit capsule in water
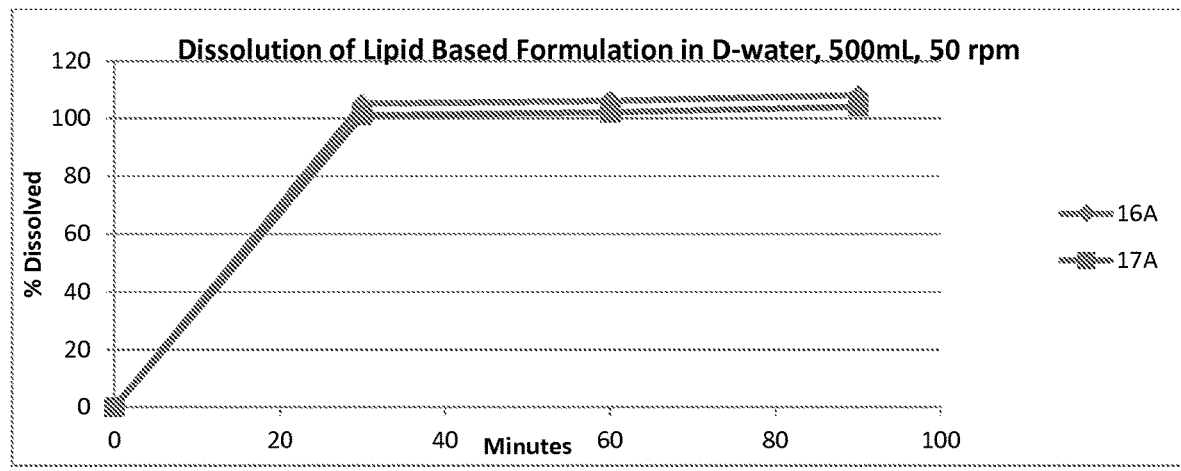

ABUSE-RESISTANT DRUG FORMULATIONS

CROSS-REFERENCE FOR PRIORITY APPLICATIONS

The present application is a national phase entry under 35 U.S.C. § 371 of International Application No. PCT/US2014/072968, filed Dec. 31, 2014, published in English, which claims priority to U.S. Provisional Application No. 61/922,158, filed Dec. 31, 2013, the disclosures of which are hereby incorporated herein by reference.

BACKGROUND OF THE INVENTION

Governmental reports state that prescription drug abuse is the fastest growing drug problem in the United States, and a survey indicated that nearly one-third of people age 12 and above who used drugs illicitly for the first time in 2009 began by the non-medical use of a prescription drug. The problem is considered to have been exacerbated by the introduction of controlled-release opioid products that contain higher amounts of their active ingredients, beginning with an oxycodone product that was approved for marketing in 1995. Reports of overdosing and death from prescription pain products, especially the controlled-release oxycodone product, began to rise sharply in the early 2000s. A need clearly exists to improve the safety of opioid drug products, by making the products less susceptible for misuse.

In January 2013, the U.S. Food and Drug Administration published a draft guidance document for the evaluation and labeling of abuse-resistant opioid products. The guidance states that opioid analgesics can be abused by: swallowing whole in excessive quantities; crushing and swallowing; crushing and inhaling nasally ("snorting"); crushing and smoking; or crushing, dissolving, and injecting. Categories of abuse-resistant formulations were described as:

1. Physical barriers to prevent chewing, crushing, cutting, grating or grinding, and chemical barriers to resist extraction of the active ingredient with common solvents such as water, alcohol, and organic liquids.
2. Agonist/antagonist combinations that interfere with, reduce, or defeat the euphoria associated with abuse.
3. Aversion agents, by incorporating a substance that produces an unpleasant effect when the dosage form is altered before ingestion, or is ingested in a high dose.
4. Delivery systems that provide abuse resistance through release characteristic design or a mode of administration.
5. Prodrugs that lack opioid activity until acted upon in the gastrointestinal system.
6. Combinations of two or more of the foregoing.

The FDA describes the science of abuse deterrence as relatively new and rapidly evolving. A few abuse-resistant opioid products are currently approved for marketing. Some of these products are OxyContin® (oxycodone hydrochloride extended-release tablets), Targiniq® (oxycodone HCL+naloxone HCL), and Embeda® (morphine sulfate and naltrexone hydrochloride). Other products such as Suboxone® and Opana ER® (oxymorphone) also purport to have abuse deterrent properties but do not have a formal claim on the label. The mechanism for abuse deterrence range from physical barriers to the use of antagonists or abuse deterrent agents. For example, the Oxycontin® product sold by Purdue Pharma is formulated to have a high hardness to resist crushing, breaking, and dissolution, and also to form a viscous hydrogel in aqueous media that inhibits passage of an extract through a needle.

In general, abusers of opioid drugs will not simply ingest more than a typical therapeutic dose, since the controlled-release formulations do not provide bursts of drug bioavailability to create the desired euphoric sensations. Rather, abuse tends to involve some physical manipulation of a dosage form, so that larger amounts of immediately available drug can be taken orally, nasally, or by intravenous injection. For this reason, the OxyContin® tablets are formed from a partially molten mixture that contains a high molecular weight polyethylene oxide excipient; the result is a tablet that is not easily powdered and cannot readily be treated to form a solution that is capable of being injected. The very high hardness of this product, however, would not permit reproducible splitting of a dosage form to administer a reduced dose or improve the administration for those having difficulty in swallowing.

Despite the availability of a few products with abuse deterrent properties, the abuse of prescription medicine is still on rise and the serious abusers can bypass the deterrent mechanism to extract the drug by more sophisticated manipulation. Novel technologies are needed so that these important classes of medicines can be made available to the patients while lowering the risk of abuse and diversion for these products. In particular, new formulations are needed which can be used with immediate release pharmaceutical products.

New formulations, while having abuse-resistant properties, must also allow for the active pharmaceutical ingredient to be soluble in the gastrointestinal tract and have the desired pharmacological activity. In the case of opioids, the pharmacological activity would be an analgesic effect.

BRIEF SUMMARY OF THE INVENTION

The present invention is directed to immediate release oral dosage forms of pharmaceutically active agents that are susceptible to abuse, and which due to abuse deterrent agents contained therein, decrease the potential for or inhibit abuse of the pharmaceutically active agent.

Aspects of the present invention provide formulations of drugs that resist attempts to administer the active ingredients by unintended routes and/or in unintended large doses. The inventive formulations contain a plurality of abuse deterrent agents that cause discomfort to the user when administered in an improper manner, make the extraction of the active ingredient from the formulation more difficult, and therefore prevent or at least significantly reduce the potential for abuse, while allowing the pharmaceutical formulation to release the active pharmaceutical ingredient in the gastrointestinal tract upon ingestion at the recommended dose to allow for the desired pharmacological effect.

A first aspect of the present invention is directed to an abuse-resistant, immediate-release liquid pharmaceutical composition, comprising a mixture of an effective amount at least one pharmaceutically active agent susceptible to abuse, an organic vehicle, a surfactant, a co-solvent, and optionally a viscosity-building polymer; wherein said organic vehicle, surfactant, and co-solvent co-elute with the pharmaceutically active agent when exposed to a solvent, and wherein the viscosity-building polymer is present in an amount that slows the release of the pharmaceutically active agent if multiple unit doses of the composition are administered.

Another aspect of the present invention is directed to a method of rendering abuse resistant an active pharmaceutical agent that is susceptible to abuse, comprising preparing an immediate-release liquid pharmaceutical composition, by mixing an effective amount of at least one pharmaceutically active agent susceptible to abuse, an organic vehicle, a surfactant, a co-solvent, and optionally, a viscosity-building polymer; wherein said organic vehicle, surfactant, and co-solvent co-elute with the pharmaceutically active agent when exposed to a solvent, and wherein the viscosity-building polymer is present in an amount that slows the release of the pharmaceutically active agent if multiple unit doses of the composition are administered.

A further aspect of the present invention is directed to a method of deterring abuse of a pharmaceutically active agent that is susceptible to abuse, comprising administering the pharmaceutically active agent susceptible to abuse to a subject in need thereof, wherein the pharmaceutically active agent is formulated in an immediate-release liquid pharmaceutical composition that comprises a mixture of an effective amount of the pharmaceutically active agent susceptible to abuse, an organic vehicle, a surfactant, a co-solvent, and optionally a viscosity-building polymer; wherein said organic vehicle, surfactant, and co-solvent co-elute with the pharmaceutically active agent when exposed to a solvent, and wherein the viscosity-building polymer is present in an amount that slows the release of the pharmaceutically active agent if multiple unit doses of the composition are administered.

BRIEF DESCRIPTION OF THE DRAWING

FIG. 1 is a graph that illustrates the in-vitro dissolution of a drug formulated with Miglyol 812, triethyl citrate, ducosate sodium and silica showing immediate release of a therapeutic agent under normal use conditions.

DETAILED DESCRIPTION

The present disclosure is directed to oral drug formulations that inhibit abuse of their active ingredient through ingestion of abnormally large quantities, or by unintended administration routes such as inhalation or injection, and resist attempts to extract a contained active ingredient as a single entity.

"Composition" as used herein refers to the drug dosage unit for administration to a patient. It may also be used in reference solely to the active ingredient, or to a formulation containing the active ingredient. In some embodiments, the composition may be in the form of an isotropic mixture.

The terms "abuse-resistant composition" or "abuse-resistant formulation" are used interchangeably herein to refer to compositions that reduce the potential for improper administration of drugs but that deliver a therapeutically effective dose when administered properly and as directed. Improper administration includes tampering with the dosage form and/or administering the drug by any route other than instructed.

The terms "drug," "active agent," and "pharmaceutically active agent" are used interchangeably herein to refer to a chemical compound that induces a desired pharmacological and/or physiological effect. The terms also encompass pharmaceutically acceptable derivatives of those active agents specifically mentioned herein, including, but not limited to, salts, solvates, hydrates, complexes with one or more molecules, prodrugs, active metabolites, lipophilic derivatives, analogs, and the like.

The term "immediate release" as used herein means that the bulk of the drug is released from the dosage form in which it is administered in the stomach. By "bulk," it is meant that at least about 50% of the drug should be released in the stomach. In many cases, that release will be as quickly as practicable, i.e., dissolution will be as close to that resulting from administering an equal amount of fine loose powder."

A "viscosity-building polymer" is used herein to refer to a chemical compound that increases the viscosity of a liquid formulation. In some cases, this may occur particularly if the formulation is tampered with. In some embodiments, the polymer forms a gel upon exposure to an aqueous environment. In some other embodiments, the viscosity building agent may provide a highly porous surface that enables the formation of a network structure resulting in increased viscosity.

The formulations of the present invention are generally liquid or semi-solid in nature, such as solutions and dispersions of various types. The term "liquid" embraces "semi-solids" and thus refers to compositions that have a measurable viscosity at room temperature. Liquid compositions are pourable and have a viscosity that generally ranges from about 1 to about 25,000 cps, whereas semi-solid compositions are non-flowable under the force of gravity and have a viscosity that generally ranges from about 25,000 to about 150,000 cps. Some of the formulations may appear to be single phase system even though at microscopic level they might not be true solutions. In some embodiments, an active agent is dissolved or dispersed in a nonaqueous matrix. In other embodiments, an active agent can be a component of one of the phases in an emulsion, a microemulsion or other dispersion having aqueous and nonaqueous phases. The liquid or semi-solid formulation can optionally be contained within a soft or hard capsule for convenience of administration.

In some embodiments, formulations of this disclosure are self-emulsifying drug delivery systems (SEDDS), which are isotropic mixtures of at least one drug, an organic oily vehicle, surfactant, solvent, and co-solvent functional ingredients. Some ingredients can perform more than one of these functions. The SEDDS form fine, relatively stable oil-in-water (o/w) emulsions in aqueous gastric fluid, under the influence of the gentle peristaltic agitation of the gastrointestinal system. The formulations of the present invention can also be self-microemulsifying drug delivery systems (SMEDDS) or self-nanoemulsifying drug delivery systems (SNEDDS), which are isotropic mixtures of at least one drug, an organic vehicle, a surfactant, and a co-solvent. These formulations rapidly form relatively stable oil-in-water (o/w) emulsions where the drug is contained in micron-size or nanometer-size droplets for SMEDDS and SNEDDS, respectively, upon aqueous dilution in gastrointestinal fluids. The formulations that are SEDDS, SMEDDS, and SNEDDS can be orally administered in soft or hard capsules, including those formed from gelatin or a substituted cellulose polymer such as hypromellose. SEDDS, SMEDDS, and SNEDDS have been used for bioavailability enhancement of some poorly absorbed drugs. It has now been discovered by the inventors that these formulations can be used as abuse-resistant formulations for drugs. In the event that the cosolvent has surfactant type properties e.g., polyglycolized glycerides, polyethylene sorbitan esters, Capmul MCM or Labrasol, they can also provide a microemulsion-type formulation matrix.

I. Pharmaceutically Active Agents

The drugs or salts thereof that have a potential to be abused or which are susceptible to abuse include, but are not limited to, those commonly prescribed for relieving pain such as barbiturates and opioids. A few specific drug compounds for pain relief include, but are not limited to, codeine, phenazocine, tilidine, tramadol, meperidine, sufentanil, prodine, methadone, pentazocine, oxycodone, oxymorphone, hydrocodone, hydromorphone, tapentadol, morphine, buprenorphine, and fentanyl. Other drugs that can be misused for non-therapeutic purposes have hallucinogenic properties or otherwise affect the central nervous system, including stimulants such as amphetamines.

Some other specific drugs that can be the subject of abuse include, without limitation thereto: alfentanil; allobarbital; allylprodine; alphaprodine; alprazolam; amfepramone; amphetamine; amphetaminil; amobarbital; anileridine; apocodeine; barbital; benzylmorphine; bezitramide; bromazepam; brotizolam; buprenorphine butobarbital; butorphanol; camazepam; carisoprodol, chlorodiazepoxide; clobazam; clonazepam; clonitazene; clorazepate; clotiazepam; cloxazolam; cocaine; codeine, cyclobarbital; cyclorphan; cyprenorphine; delorazepam; desomorphine; dextroamphetamine, dexmethylphenidate, dextromoramide; dextropropoxyphen; dezocine; diampromide; diamorphone; diazepam; dihydrocodeine; dihydromorphine; dimenoxadol; dimepheptanol; dimethylthiambutene; dioxaphetyl butyrate; dipipanone; dronabinol; eptazocine; ephedrine, estazolam; eszopiclone, ethoheptazine; ethylmethylthiambutene; ethyl loflazepate; ethylmorphine; etonitazene; etorphine; fencamfamine; fenethylline; fenproporex; fentanyl, fludiazepam; flunitrazepam; flurazepam; halazepam; haloxazolam; heroin; hydrocodone, hydromorphone, hydroxypethidine; hydroxymethyl morphinane; isomethadone; ketazolam; ketobemidone; levomethadyl acetate; levomethadone; levorphanol; levophenacylmorphane; lofentanil; loprazolam; lorazepam; lormetazepam; mazindol; medazepam; mefenorex; meprobamate; meptazinol; metazocine; methadone, methylmorphine; methamphetamine; methaqualone; methylphenidate; methylphenobarbital; methyprylon; meperidine, metopon; midazolam; modafinil; morphine, myrophine; nabilone; nalbuphine; nalorphine; narceine; nicomorphine; nimetazepam; nitrazepam; nordazepam; norlevorphanol; normethadone; normorphine; norpipanone; opium; oxazepam; oxazolam; oxycodone, oxymorphone, pernoline; pentazocine, pentobarbital; pethidine; phenadoxone; phenomorphan; phenoperidine; piminodine; pholcodine; phenmetrazine; phenobarbital; phentermine; phenazocine, pinazepam; pipradrol; piritramide; prazepam; prodine, profadol; proheptazine; promedol; properidine; propoxyphene; pseudoephedrine, remifentanil; secbutabarbital; secobarbital; sufentanil, tapentadol, temazepam; tetrazepam; tilidine; tramadol; triazolam; vinylbital and zolpidem. The drugs include any pharmacologically active stereoisomeric compounds, as well as derivatives of the base drug such as esters and salts, including any solvates thereof. The pharmaceutically active agent is present in the formulation in an amount effective for the intended therapeutic purpose. These amounts are well known in the art. Indeed, all of the active agents embraced by the present invention are known per se, as are the doses at which they can be given safely and effectively for the intended therapeutic purpose.

In addition to the pharmaceutically active agent susceptible to abuse, the formulation may include another pharmaceutically active agent such as an analgesic. Examples of analgesics include, but are not limited to, acetaminophen, aspirin, non-steroidal anti-inflammatory drugs, ibuprofen, naproxen, diclofenac, celecoxib, and paracetamol. In some embodiments, e.g., when the formulation is in the form of capsule, the analgesic may be present as part of a solution or a dispersion of the fill material in a pharmaceutically effective amount. In some embodiments, acetaminophen may be present as part of a solution or a dispersion of the fill material in a range of about 0.01 g/g (or 1% w/w) to about 0.35 g/g (or 35%/w/w). In some embodiments, a dispersion comprising the analgesic is coated onto the capsule shell in a pharmaceutically effective amount. In another embodiment, a dispersion comprising acetaminophen is coated onto the capsule shell in an amount of about 225 mg to about 325 mg per shell. In some embodiments, the coating dispersion is prepared by dispersing a micronized analgesic in a hypromellose (HPMC)-based coating system, or a polyvinyl alcohol (PVA) coating system (e.g., Opadry®) in water. The coating of the capsules may be performed in a pan coating machine.

II. Abuse Deterrent Agents

The inventive formulations impart abuse deterrent characteristics by any number of mechanisms when the product is used in an unintended manner. This can occur for example, if a dosage form of the present invention is manipulated prior to ingestion or if the patient takes multiple dosage forms of the invention resulting in a higher total dose than intended by the prescriber. In some embodiments, the abuse deterrent agents comprise an organic vehicle, a co-solvent, and a surfactant.

Abuse-resistant formulations can be obtained using combinations of excipients that individually impart various properties to deter tampering or unintended administration. For example, combinations containing an organic vehicle, co-solvent, and surfactant ingredients affect the abuse potential in different ways to yield useful drug formulations. Various types of the drug abuse deterrent agents, in a formulation can be categorized as tissue irritants and gastrointestinal irritants when consumed in large doses or manipulated for an unintended route of administration. In some embodiments, the abuse deterrent agents co-elute with the drug in either organic solvents or aqueous media and therefore prevent a user from extracting out the drug by itself. Alternatively if the formulations are thermally treated i.e., heated or refrigerated, the excipients and drug will remain together as part of the matrix. The effects that are obtainable with combinations of the abuse deterrent agents in a formulation include the following, for different administration routes:

1. Nasal Route: Due to severe nasal irritation with unpleasant odor, the abuse deterrent agents in the formulation will result in noxious effects upon insufflation when the product is manipulated for administration by the nasal route. Due to both high boiling points and good solubilization properties of ester-type oils, the formulation will deter abusers from vaporizing for inhalation, as the vaporization temperatures are relatively high and can induce degradation of drug and/or excipients, thus inhibiting pharmacological effects to an abuser.

2. Oral Route: Due to their surface active properties, surfactants can cause adverse effects of laxatives, if large enough quantities of the formulation are ingested. Furthermore, for the compositions containing an opioid receptor antagonist (as described hereinbelow), the lipid and surfactant based formulation may improve the bioavailability of antagonist that may reduce the liking of the product by the abuser. The amount of surfactant can be adjusted so that a laxative dose will not be delivered when a normal therapeutic dose of the drug is ingested. If consumed in very large doses, the viscosity building polymer if contained in the formulation can also lower the release of drug by forming a viscous gel in the gastrointestinal fluids.

3. Injection Route: Due to their surface active properties, surfactants can cause deterrent effects, such as tissue irritation and pain at sites of injection. Furthermore, the viscosity building agents in the product will limit the ability to syringe the material for injection purpose either "as is" or after extracting with aqueous vehicles.

The abuse resistant formulations are designed not to contribute any adverse effects when administered at the recommended doses of the contained drugs therein; however they will produce noxious effects upon manipulation via nasal and injection routes of administration, and oral ingestion of excessive quantities.

Embodiments of the formulations provide immediate release of their contained drug components into gastric fluid, upon dissolution of the capsule shell. These formulations (that are in the form of a capsule) are not intended to provide a delayed or prolonged bioavailability of the drug component.

In some embodiments, the drug may be present in microencapsulated form to provide extended release products.

Lists of pharmaceutical excipients herein are not intended to be exhaustive, but merely represent the types of materials that are useful. Also, when a particular product and supplier are mentioned, in many cases similar products are available commercially from other suppliers and also can be used.

II.a. Organic Vehicles

Pharmaceutically acceptable organic vehicles that are useful include but are not limited to C6-C18 fatty acids and esters thereof, fatty acid glycerides (e.g., C6-C18 fatty acid mono-, di- and tri-glycerides), C6-C18 fatty acid propylene glycol mono- and di-esters, C6-C18 fatty acid polyethylene glycol ("PEG") esters, animal and vegetable oils (e.g., fish oil, emu oil, soyabean oil, cottonseed oil, almond oil, corn oil, sesame oil, castor oil, safflower oil, olive oil, canola oil, sunflower oil, and flax oil), individually or in any combination of two or more, and others. Some oils may be hydrogenated or non-hydrogenated. The HLB values of the organic vehicles are in a range of about 1 to about 10. The organic vehicle is present in an amount that results in discomfort to the abuser when the organic vehicle is co-eluted with the pharmaceutically active agent, as described herein. The organic vehicle may be present in an amount that generally ranges from about 0.5 g/g (or 50% w/w) to about 0.9 g/g (or 90%/w/w), and in some embodiments from about 60 to about 70% w/w. Table 1 below lists certain representative organic vehicles.

TABLE 1

Representative Organic Vehicles

| Organic Vehicle | Trade Name/Supplier |
| --- | --- |
| Caprylic acid | Several names and suppliers |
| Capric acid | Several names and suppliers |
| Oleic acid | Several names and suppliers |
| Palmitic acid | Several names and suppliers |
| Glyceryl monooleate | CAPMUL ® GMO-50/Abitec |
| Glyceryl monocaprylate | CAPMUL MCM C8/Abitec |
| Glyceryl monocaprate | CAPMUL MCM C10/Abitec |
| Glyceryl caprylate/caprate | CAPMUL MCM/Abitec |
| Propylene glycol monocaprylate | CAPMUL PG-8/Abitec |
| Propylene glycol monolaurate | CAPMUL PG-12/Abitec |
| Propylene glycol dilaurate | CAPMUL PG-2L Abitec |
| PEG-4 glyceryl caprylate/caprate | LABRAFAC ® Hydro WL 1219/Gattefosse |
| PEG-6 glyceryl linoleate | LABRAFIL ® M 2125 CS/Gattefosse |
| PEG-6 glyceryl oleate | LABRAFIL M 1944 CS/Gattefosse |
| Caprylic/Capric Triglyceride | Miglyol 812/Sasol |
| Propylene Glycol Dicaprylate/Dicaprate | Miglyol 840/Sasol |

These substances are generally soluble in organic solvents and therefore can be co-eluted with drug substances that also are soluble in the solvents. The organic vehicles can cause irritation of nasal mucosa if inhaled, and will cause irritation at an injection site, thereby deterring misuse involving administration by these routes. In addition, ingesting large quantities of the organic vehicles will result in adverse gastrointestinal effects, such as upset stomach or diarrhea.

II.b. Co-Solvents

Representative co-solvents include ingredients such as liquid esters, e.g., triethyl citrate, glycerine, acetyl triethyl citrate, acetyl tributyl citrate, dibutyl sebacate, propylene glycol, polyethylene glycols, triacetin, and diethylene glycol monoethyl ether. The dielectric constant values of the co-solvents are in a range of about 5 to about 50. The co-solvents have solubility in both aqueous media and organic solvents, so would be co-eluted together with a drug if extraction from the formulation is attempted. They can also function in a formulation to improve solubility of a drug in an organic oil, particularly when the drug is being used in the form of a salt. Some of these ingredients may cause tissue irritation and/or unpleasant gastrointestinal effects. The co-solvent is present in an amount that results in discomfort to the user when the co-solvent is co-eluted with the pharmaceutically active agent, as described herein. The co-solvent may be present in an amount that generally ranges from about 0.1 g/g (or 10% w/w) to about 0.5 g/g (or 50%/w/w), and in some embodiments from about _10%_ to about _ 20%_ % w/w.

II.c. Surfactants

Pharmaceutically acceptable surfactants that are useful in the practice of the present invention have solubility in oils, co-solvents, or aqueous media. The surfactant component helps in modulating the solubility of the compound as well in reducing the abuse potential by a dual mechanism. First, it elicits the irritant response when administered "as is" by nasal or injection routes, and second, by co-eluting with the drug when extracted with the commonly used solvents such as aqueous and organic solvents. Surfactants produce tissue irritation when applied to nasal mucosa and will cause local irritation at an injection site. Further, docusate sodium is commonly used as a stool softener/laxative, so while providing some relief for opioid-induced constipation at the intended dose, it can cause undesirable gastrointestinal effects if large quantities are ingested. Similar gastrointestinal effects can be obtained by ingesting other surfactants. The surfactant is present in an amount that results in discomfort to the abuser when the surfactant is co-eluted with the pharmaceutically active agent, as described herein. The HLB values of the surfactants are in a range of about 4 to about 30.

Types of surfactants that may be useful in the practice of the present invention include non-ionic surfactants e.g., esters of fatty acids, especially of C8-C24 and preferably of C16-C22, and fatty acid esters of polyols such as glycerol or sorbitol; sorbitan fatty acid esters ethoxylated with from 2 to moles of ethylene oxide; polyethylene glycol fatty acid esters; polyethyleneglycol esters and polyethyleneglycol ethers; and ethoxylated carboxylic acids (e.g., PEG-35 castor oil, PEG-40 castor oil, steareth-2 (Brij 72, Uniqema), steareth-21 (Brij 721, Uniqema), ceteareth-25 (Cremophor A25, BASF Cooperation), PEG-7 hydrogenated castor oil (Cremophor W07, BASF Cooperation), and PEG-30 Dipolyhydroxystearate (Arlacel P 135, Uniqema)). Anionic surfactants e.g., alkyl ether sulfates and sulfosuccinates, may also be useful. Alternatively cationic and amphoteric surfactants such as phospholipids, lysophospholipids, and pegylated phospholipids may also be used.

Yet other surfactants that may be useful include PEGylated derivatives of vitamin E. Examples include tocopherol PEG succinate, tocopheryl polyethylene glycol sebacate, tocopheryl polyethylene glycol dodecanodioate, tocopheryl polyethylene glycol suberate, tocopheryl polyethylene glycol azelaate, tocopheryl polyethylene glycol citraconate, tocopheryl polyethylene glycol methylcitraconate, tocopheryl polyethylene glycol itaconate, tocopheryl polyethylene glycol maleate, tocopheryl polyethylene glycol glutarate, tocopheryl polyethylene glycol glutaconate, tocopheryl polyethylene glycol fumarate, tocopheryl polyethylene glycol phthalate, tocotrienol polyethylene glycol succinate, tocotrienol polyethylene glycol sebacate, tocotrienol polyethylene glycol dodecanodioate, tocotrienol polyethylene glycol suberate, tocotrienol polyethylene glycol azelaate, tocotrienol polyethylene glycol citraconate, tocotrienol polyethylene glycol methylcitraconate, tocotrienol polyethylene glycol itaconate, tocotrienol polyethylene glycol maleate, tocotrienol polyethylene glycol glutarate, tocotrienol polyethylene glycol glutaconate, tocotrienol polyethylene glycol fumarate and tocotrienol polyethylene glycol phthalate. (See, e.g., U.S. 20140271593.)

Some representative examples of specific surfactants are listed in Table 2 below.

TABLE 2

Representative Surfactants

| Surfactant | Trade Name/Supplier |
|---|---|
| Dioctyl sodium sulfosuccinate (docusate sodium or DOSS) | Many names and suppliers |
| Sodium lauryl sulfate | Many names and suppliers |
| PEG-32 glyceryl laurate | GELUCIRE ® 44/14/Gattefosse ACCONON ® C-44/Abitec |
| PEG-32 glyceryl palmitostearate | GELUCIRE 50/13/Gattefosse |
| PEG-35 castor oil (polyoxyl 35 ricinoleate castor oil) | CREMOPHOR EL/BASF ETOCAS ® 35 NF/Croda |
| PEG-8 glyceryl caprylate/caprate | LABRASOL ®/Gattefosse ACCONON MC-8/Abitec |
| PEG-6 glyceryl caprylate/caprate | SOFTIGEN ® 767/Sasol ACCONON CC-6/Abitec |
| PEG-40 hydrogenated castor oil (PEG-40 hydrogenated ricinoleate) | CREMOPHOR RH 40/BASF |
| Macrogol 15 hydroxystearate (polyoxyl 15 hydroxystearate) | SOLUTOL ® HS15/BASF |
| Block copolymers based on ethylene oxide and propylene oxide | PLURONIC ® (e.g., 188 or 407)/BASF |
| Polyoxyethylene 20 sorbitan monolaurate (polysorbate 20) | TWEEN ® 20/ICI Americas |
| Polyoxyethylene 20 sorbitan monooleate (polysorbate 80) | TWEEN 80/ICI Americas |
| Sorbitan monolaurate | SPAN ® 20/Croda |
| Sorbitan monooleate | SPAN 40/Croda |
| Tocopherol PEG succinate (vitamin E TPGS) | Many names and suppliers |
| Polyoxyl 40 stearate | MYRJ ® 52/Croda |

The surfactant may be present in an amount that generally ranges from about 0.01 g/g (or 1% w/w) to about 0.4 g/g (or 40%/w/w), and in some embodiments from about 2 to about 10% w/w.

Abuse-resistant effects of certain combinations of abuse deterrent agents in a formulation are summarized in Table 3. More generally, combinations of organic vehicles, surfactants and/or cosolvents that exhibit the desired abuse deterrent properties may be selected in accordance with standard techniques in the art with respect to criteria that may include tissue irritation preventing snorting, gastrointestinal disturbances at very high doses, unpleasant odor or taste, and difficulty in syringeability.

TABLE 3

Examples of Combinations of Abuse Deterrent Agents

| | Solubility | | Abuse Resistance | | |
|---|---|---|---|---|---|
| Combination | Water | Solvents | Oral | Injection | Nasal |
| Glyceryl caprylate/caprate + docusate sodium | Yes | Yes | Yes | Yes | Yes |
| Glyceryl caprylate/caprate + triethyl citrate (TEC) | Yes | Yes | Yes | Yes | Yes |
| Propylene glycol monocaprylate + triethyl citrate | Yes | Yes | Yes | Yes | Yes |
| Propylene glycol monocaprylate + docusate sodium | Yes | Yes | Yes | Yes | Yes |
| Propylene glycol + docusate sodium | Yes | Yes | Yes | Yes | Yes |
| Propylene glycol + triethyl citrate | Yes | Yes | Yes | Yet | Yes |
| PEG-400 + docusate sodium | Yes | Yes | Yes | Yes | Yes |
| PEG-400 + triethyl citrate | Yes | Yes | Yes | Yes | Yes |

III. Viscosity-Building Polymer

Abuse-resistant formulations also preferably have a viscosity that inhibits injection, by not permitting a rapid transit through a hypodermic needle with the typically applied forces on a syringe plunger. The viscosity can significantly affect the efforts required for nasal administration of these formulations as well. The viscosity-building polymers or additional viscosity-building agents (described hereinbelow) can also work as absorption retardants when a drug is ingested in overdose quantities.

Techniques for increasing viscosity include incorporating a viscosity-building polymer in a formulation. In some embodiments, the polymer will form an aqueous gel when exposed to an aqueous environment. Certain hydrophilic polymers, such as polyethylene oxides, can form viscous gels when extracted into aqueous media and these will not have adequate "syringeability" to permit injection. Examples of useful polyethylene oxide polymers that are sold as POLYOX® by The Dow Chemical Co. are listed in Table 4 below (wherein the superscripts a, b and c refer to 5%, 2% and 1% solutions, respectively, measured at 25° C. using a Brookfield viscometer in accordance with the manufacturer's instructions).

TABLE 4

Representative Viscosity-Building Polymer

| Trade Name | INCI Name | Approx. Molecular Weight (g/mole) | Viscosity (mPa · s) |
|---|---|---|---|
| POLYOX WSR-205 | PEG-14M | 600,000 | about 4500-about 8800$^a$ |
| POLYOX WSR-301 | PEG-90M | 4,000,000 | about 1650-about 5500$^c$ |
| POLYOX WSR N-10 | PEG-2M | 100,000 | about 12-about 50$^a$ |
| POLYOX WSR N-80 | PEG-5M | 200,000 | about 65-about 115$^a$ |
| POLYOX WSR N-750 | PEG-7M | 300,000 | about 600-about 1,000$^a$ |
| POLYOX WSR N-3000 | PEG-14M | 400,000 | about 2250-about 4500$^a$ |

TABLE 4-continued

Representative Viscosity-Building Polymer

| Trade Name | INCI Name | Approx. Molecular Weight (g/mole) | Viscosity (mPa · s) |
|---|---|---|---|
| POLYOX WSR N-12K | PEG-23M | 1,000,000 | about 400-about 800[b] |
| POLYOX WSR N-60K | PEG-45M | 2,000,000 | about 200-about 400[b] |

Other useful viscosity-building polymers include, without limitation, polysaccharides such as pectin, crosslinked starches, sodium carboxymethycellulose, and gums such as xanthan gum, as well as silicone polymers, carbomers (e.g., carbopol 934P NF, carbopol 974P NF and carbopol 971P NF, available from Noveon Pharmaceuticals), and polycarbophil tragacanth. The hydrodynamic volume and swelling capacity of anionic polymers, such as carbomers, increase sharply when the carboxylic groups become ionized at a pH of about 6. In another embodiment, the highest plateau in viscosity is achieved in a pH range of about 6 to about 7. Therefore, buffering agents or alkalizing agents can also be used to promote the gelling of carbomers with good buffering capacity which contributes to maintenance of the desired pH and provides high viscosity at low concentrations of polymer. Representative examples of buffering agents are sodium carbonate, sodium bicarbonate, sodium acetate, potassium dibasic phosphate, sodium dibasic phosphate (and mixtures of two or more thereof). Representative examples of alkalizing agents are magnesium oxide, aluminium oxide, calcium oxide, calcium carbonate, calcium bicarbonate, Tris (hydroxymethyl aminomethane) (and mixtures of two or more thereof).

The viscosity-building polymer is present in an amount that results in gelling when the polymer is exposed to aqueous media, as described herein, and prevents a user from injecting the formulation using a hypodermic needle. In some embodiments, the viscosity-building polymer is present in an amount that does not slow down the drug release from a single dose administration, but does slow down the drug release from multiple unit dose administration. The viscosity-building polymer may be present in an amount that generally ranges from about 0.005 g/g (or 0.5% w/w to about 0.2 g/g (or 20%/w/w), and in some embodiments from about 1% to about 10% % w/w. In some embodiments, the buffering agents or alkalizing agents may be present in a range of about 0.005 g/g (or 0.5% w/w) to about 0.1 g/g (or 10%/w/w), and in some embodiments from about 1% to about 5% w/w.

Formulations such as SEDDS, SMEDDS or SNEDDS typically provide a rapid drug release in the GI tract when taken as a single dose. The amount of viscosity-building polymer per unit dose is selected so as not to retard the drug release from a single dose administration, but will retard the drug release from multiple unit dose administration. This is due to the fact that viscosity and gel strength of the polymer are drastically increased when exposed to the GI tract at higher concentrations from multiple doses, diminishing dispersibility of self-emulsifying, self-microemulsifying and self-nanoemulsifying formulations. The drug is eventually entrapped in the polymer gel matrix and is no longer able to provide an immediate release of action to abuser from overdose manipulation. The rate of rise of drug concentration is thought to contribute to differential abuse potential among drugs, formulations, and routes of administration. In this case, ingestion of increasing quantities of the formulation will not proportionally increase in maximum concentration ($C_{max}$) to reach a full potential of drug-liking effects (e.g., euphoria, sedation and relaxation) of the opioid. In addition, it will take a longer time to reach maximum concentration ($T_{max}$). The result will be a reduced desirability of deliberately overdosing the drug.

IV. Other Additives

In some embodiments, formulations will contain only organic vehicle, co-solvent, surfactant, and viscosity-building polymer ingredients, in addition to a drug. However, other excipients can be included as desired, including, for example, one or more of antioxidants, additional viscosity-building agents, coloring agents, flavoring agents, sweeteners, or a mixture thereof.

Examples of antioxidants include, but are not limited to, α-tocopherol, trolox, butylated hydroxytoluene, butylated hydroxyanisole, propyl gallate, or a mixture thereof, which are effective to inhibit the oxidation of lipids and polyethylene oxides, thereby improving oxidative stability for certain drugs. The antioxidant may be present in an amount that generally ranges from about 0.0001 g/g (or 0.01% w/w) to about 0.01 g/g (or 2%/w/w) and in some embodiments from about 0.1% to about 1% w/w.

Examples of additional viscosity-building agents include, but are not limited to, colloidal silicon dioxide (e.g., Aerosil 200), fumed silica (e.g., Cab-O-Sil), mesoporous silica or a mixture thereof, which can also be used as an effective viscosity-building agent to create more viscous gels of the formulation. The viscosity-building agent may be present in an amount that generally ranges from about 0.02 g/g (or 2% w/w) to about 0.2 g/g (or 20%/w/w). Drugs can be pretreated with silica to capture the drug on to the microstructure such as in mesoporous silica to further reduce the efficiency of extraction during sample manipulation for abuse.

In addition to the pharmaceutically active agent susceptible to abuse, the formulation may further include an opioid receptor antagonist such as naloxone, naltrexone, methyl naltrexone or salts thereof in either dissolved or dispersed state. These agents interfere with the euphoric effect caused by the drug. The presence of the ingredient reduces the risk of abuse by nasal or intravenous routes. Likewise, the presence of an opioid receptor antagonist in a liquid formulation, wherein bioavailability of the opioid receptor antagonist such as naloxone may be increased, further reduces the liking of the product when abused by oral route such as ingesting multiple units. In some embodiments the antagonist agent may be present in 0.5% to 10% w/w, either "as is" or in sequestered form. The antagonist may be included in the formulation in a sequestered form that becomes activated only if the product is manipulated.

The following examples further describe certain specific aspects and embodiments of the disclosure, but should not be construed as limiting the scope of the disclosure in any manner.

Example 1

The formulations described in Tables 5 and 6 may be made following the following protocols.

TABLE 5

Abuse-resistant formulations

| Ingredient | mg/Capsule | | |
|---|---|---|---|
| (Function) | 1A | 1B | 1C |
| Oxycodone (Pharmaceutically Active Agent) | 10 | — | — |
| Oxymorphone (Pharmaceutically Active Agent) | — | 10 | — |
| Tramadol (Pharmaceutically Active Agent) | — | — | 10 |
| α-Tocopherol (antioxidant) | 1.5 | 1.5 | 1.5 |
| Dioctyl sodium sulfosuccinate (surfactant) | 10-25 | 10-25 | 10-25 |
| PEG-90M* (viscosity-building polymer) | 20 | 20 | 20 |
| PEG-400 (co-solvent) | 50 | 50 | 50 |
| Propylene glycol monocaprylate** (organic vehicle) | q.s. to 400 | q.s. to 400 | q.s. to 400 |

*e.g., POLYOX WSR-301, a product of The Dow Chemical Co.
**e.g., CAPMUL PG-8, a product of ABITEC.

The formulations are prepared by combining PEG-400 and propylene glycol monocaprylate with mixing at 50-60° C., dissolving α-tocopherol in the mixture at the same temperatures, and then dissolving the drug and dioctyl sodium sulfosuccinate while maintaining the temperature. The mixture is cooled to ambient temperature, and then PEG-90M is dispersed in the mixture. The final mixture is filled into capsules.

Example 2

Abuse-resistant formulations are prepared, using the ingredients listed in Table 6 below.

TABLE 6

Abuse-resistant formulations

| Ingredient | mg/Capsule | | |
|---|---|---|---|
|  | 2A | 2B | 2C |
| Oxycodone (Pharmaceutically Active Agent) | 10 | — | — |
| Oxymorphone (Pharmaceutically Active Agent) | — | 10 | — |
| Hydrocodone (Pharmaceutically Active Agent) | — | — | 10 |
| α-Tocopherol (Antioxidant) | 1.5 | 1.5 | 1.5 |
| PEG-40 hydrogenated castor oil* (Surfactant) | 10-25 | 10-25 | 10-25 |
| PEG-14M** (Viscosity-building polymer) | 20 | 20 | 20 |
| PEG-400 (Co-solvent) | 50 | 50 | 50 |
| Glyceryl monocaprylate† (organic vehicle) | q.s. to 400 | q.s. to 400 | q.s. to 400 |

*e.g., CREMOPHOR RH-40, a product of BASF.
**e.g., POLYOX WSR-205, a product of The Dow Chemical Co.
†e.g., CAPMUL MCM C8, a product of ABITEC.

The formulations are prepared by combining PEG-400 and glyceryl monocaprylate with mixing at 50-60° C., dissolving α-tocopherol in the mixture at the same temperature, and then dissolving the drug and PEG-40 hydrogenated castor oil while maintaining the temperature. The mixture is then cooled to ambient temperature, and then PEG-14M is dispersed in the mixture. The final mixture was filled into capsules.

Example 3

Abuse-resistant formulations (dispersed drug) were prepared using the ingredients listed in Table 7 below.

TABLE 7

Abuse-resistant formulations

| Ingredient | mg/Capsule | | |
|---|---|---|---|
|  | 3A | 3B | 3C |
| Oxycodone (Pharmaceutically Active Agent) | 10 | — | — |
| Oxymorphone (Pharmaceutically Active Agent) | — | 10 | — |
| Hydrocodone (Pharmaceutically Active Agent) | — | — | 10 |
| α-Tocopherol (Antioxidant) | 1.5 | 1.5 | 1.5 |
| Dioctyl sodium sulfosuccinate | 10-25 | 10-25 | 10-25 |
| Colloidal silica | 20 | 20 | 20 |
| Triethyl citrate (co-solvent) | 5-20 | 5-20 | 5-20 |
| Soyabean Oil† (organic vehicle) | q.s. to 400 | q.s. to 400 | q.s. to 400 |

*e.g., CREMOPHOR RH-40, a product of BASF.
**e.g., POLYOX WSR-205, a product of The Dow Chemical Co.
†e.g., Oil, WHC product The formulations were prepared by combining soyabean oil and alpha tocopherol, triethyl citrate and dioctyl sodium sulfosuccinate to obtain a clear solution. Drug was slowly added to the solution while continuously mixing the dispersion (low shear or high shear homogenization). The mixing mechanism should provide uniform distribution of drug in the vehicle and at desired particle size to ensue physical and chemical stability. Then colloidal silica was added until uniform dispersion was obtained while continuously mixing. The final mixture was filled into hard gelatin, soft gelatin or hypromellose-based capsules.

Example 4

Abuse-resistant formulations (dispersed drug) were prepared, using the ingredients listed in Table 8 below.

TABLE 8

Abuse-resistant formulations

| Ingredient | mg/Capsule | | |
|---|---|---|---|
|  | 4A | 4B | 4C |
| Oxycodone (Pharmaceutically Active Agent) | 10 | — | — |
| Oxymorphone (Pharmaceutically Active Agent) | — | 10 | — |
| Hydrocodone (Pharmaceutically Active Agent) | — | — | 10 |
| α-Tocopherol (Antioxidant) | 1.5 | 1.5 | 1.5 |
| Dioctyl sodium sulfosuccinate | 10-25 | 10-25 | 10-25 |
| Silica | 20 | 20 | 20 |
| Triethyl citrate (co-solvent) | 5-20 | 5-20 | 5-20 |
| Miglyol 812 (organic vehicle)† | q.s. to 400 | q.s. to 400 | q.s. to 400 |

*e.g., CREMOPHOR RH-40, a product of BASF.
**e.g., Silica could be chosen from fumed silica (Aerosil from Evonik or Syloid 244fp from Grace), mesoporous silica (Syloid XDP from Grace) or precipitated silica.
†e.g., Oil, a product of Sasol, or Oleic acid (NOF product).

The formulations were prepared by combining Miglyol 812, alpha tocopherol, triethyl citrate and dioctyl sodium sulfosuccinate to obtain a uniform solution. Drug was slowly added to this while continuously mixing the dispersion using high shear homogenization. The mixing mechanism should provide uniform distribution of drug in the vehicle and at desired particle size to ensure physical and chemical stability. Then colloidal silica was added until a uniform dispersion was obtained while continuously mixing. The final mixture was filled into capsules either hard gelatin, soft gelatin or hypromellose-based capsules.

Example 5

In an alternate embodiment of the Example 4, the opioid solution was first impregnated onto silica particularly mesoporous silica which was then dispersed in the vehicle containing oil, surfactant, co-solvent and additional viscosity building agent. This technique can further add to the abuse deterrent properties as the release of drug from the mesoporous silica can be rate-limiting. These formulations were tested for dissolution characteristics to simulate the actual usage for therapeutic benefit and the results are shown in FIG. 1. Thereafter, these formulations were tested for extraction with water as well as 40% ethanolic solution for 30 minutes at ambient conditions and tested for the extraction of drug along with surfactant and cosolvent to simulate the abuse conditions by extraction with commonly used solvents. The samples were observed visually and tested by HPLC.

A more specific example of the two formulations made using naloxone hydrochloride as model drug to represent a drug is shown in Table 9.

TABLE 9

Composition of Prototype Formulations

| Component | 16A (suspended in oil) | 17A (pre-processed with silica 1:1) |
|---|---|---|
| Naloxone HCl | 10 | 10 |
| alpha-tocopherol | 1.5 | 1.5 |
| DOSS | 25 | 25 |
| TEC | 20 | 20 |
| Silica | 25 | 15 |
| Miglyol 812 qs. To | 400 | 400 |

The in-vitro dissolution results showing the drug release in therapeutic condition is shown in FIG. 1.

The extraction results are summarized in Table 10.

TABLE 10

Co-extraction of TEC and DOSS with drug when manipulated with extraction solvents

| Batch | Media | Drug:media | % Drug extracted | % TEC extracted | % DOSS extracted |
|---|---|---|---|---|---|
| P14K081016A | Water | 1:5 | 46.0 | 68.0 | 70.0 |
| | | 1:10 | 39.7 | 81.2 | 75.5 |
| | | 1:25 | 40.4 | 91.1 | 67.2 |
| | 40% Ethanol | 1:5 | 93.8 | 79.0 | 80.8 |
| | | 1:10 | 41.7 | 85.2 | 75.5 |
| | | 1:25 | 100.5 | 96.5 | 88.5 |
| P14K081017A | Water | 1:5 | 42.1 | 66.0 | 69.7 |
| | | 1:10 | 39.4 | 81.7 | 70.8 |
| | | 1:25 | 32.9 | 89.7 | 68.4 |
| | 40% Ethanol | 1:5 | 72.2 | 76.6 | 84.3 |
| | | 1:10 | 72.7 | 88.3 | 89.5 |
| | | 1:25 | 75.9 | 92.9 | 89.3 |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An abuse-resistant liquid pharmaceutical composition comprising an immediate release unit dose of a mixture of an effective amount of at least one pharmaceutically active agent susceptible to abuse, an organic vehicle, a surfactant, a co-solvent, and a viscosity-building polymer;
   wherein the organic vehicle, surfactant, and co-solvent co-elute with the pharmaceutically active agent when exposed to a solvent;
   wherein the organic vehicle is a C6-C18 fatty acid, a C6-C18 fatty acid mono-, di- or tri-glyceride, a C6-C18 fatty acid propylene glycol mono- or di-ester, a C6-C18 fatty acid polyethylene glycol ester, a vegetable oil, or a mixture of two or more thereof, and is present in an amount of about 50% to about 90% by weight, based on the total weight of the composition;
   wherein the surfactant is dioctyl sodium sulfosuccinate, sodium lauryl sulfate, PEG-32 glyceryl laurate, PEG-32 glyceryl palmitostearate, PEG-35 castor oil, PEG-8 glyceryl caprylate/caprate, PEG-6 glyceryl caprylate/caprate, PEG-40 hydrogenated castor oil, Macrogol 15 hydroxystearate, an ethylene oxide/propylene oxide block copolymer, polyoxyethylene 20 sorbitan monolaurate, polyoxyethylene 20 sorbitan monooleate, sorbitan monolaurate, sorbitan monooleate, tocopherol PEG succinate, polyoxyl 40 stearate, or a mixture of two or more thereof, and is present in an amount of about 2% to about 40% by weight, based on the total weight of the composition;
   wherein the viscosity-building polymer is PEG-2M, PEG-5M, PEG-7M, PEG-14M, PEG-23M, PEG-45M, PEG-90M, or a combination of two or more thereof, and is present in an amount of about 0.5% to about 20% by weight, based on the total weight of the composition, so that it does not slow an immediate release of the pharmaceutically active agent from a single unit-dose administration, but slows the immediate release of the pharmaceutically active agent from a multiple unit-dose administration.

2. The pharmaceutical composition of claim 1, wherein the pharmaceutically active agent susceptible to abuse is an opioid, a barbiturate or an amphetamine.

3. The pharmaceutical composition of claim 1, wherein the pharmaceutically active agent susceptible to abuse is selected from the group consisting of codeine, phenazocine, tilidine, tramadol, meperidine, sufentanil, prodine, methadone, pentazocine, oxycodone, oxymorphone, hydrocodone, hydromorphone, tapentadol, morphine, buprenorphine, and fentanyl, or a pharmaceutically acceptable salt, ester or solvate thereof.

4. The pharmaceutical composition of claim 1, wherein the pharmaceutically active agent susceptible to abuse is selected from the group consisting of alfentanil, allobarbital, allylprodine, alphaprodine, alprazolam, amfepramone, amphetamines, amphetaminil, amobarbital, anileridine, apocodeine, barbital, benzylmorphine, bezitramide, bromazepam, brotizolam, butobarbital, butorphanol, camazepam, chlorodiazepoxide, clobazam, clonazepam, clonitazene, clorazepate, clotiazepam, cloxazolam, cocaine, cyclobarbital, cyclorphan, cyprenorphine, delorazepam, desomorphine, dextromoramide, dextropropoxyphen, dezocine, diapromide, diamorphone, diazepam, dihydrocodeine, dihydromorphine, dimenoxadol, dimepheptanol, dimethylthiambutene, dioxaphetyl butyrate, dipipanone, dronabinol, eptazocine, estazolam, ethoheptazine, ethylmethylthiambutene, ethyl loflazepate, ethylmorphine, etonitazene, etorphine, fencamfamine, fenethylline, fenproporex, fludiazepam, flunitrazepam, flurazepam, halazepam, haloxazolam, heroin, hydroxypethidine, hydroxymethyl morphinane, isomethadone, ketazolam, ketobemidone, levomethadyl acetate, levomethadone, levorphanol, levophenacylmorphane, lofentanil, loprazolam, lorazepam, lormetazepam, mazindol, medazepam, mefenorex, meprobamate, meptazinol, metazocine, methylmorphine, methamphetamine, methaqualone, methylphenidate, methylphenobarbital, methyprylon, metopon, midazolam, modafinil, myrophine, nabilone, nalbuphine, nalorphine, narceine, nicomorphine, nimetazepam, nitrazepam, nordazepam, nor levorphanol, normethadone, normorphine, norpipanone, opium, oxazepam, oxazolam, pemoline, pentobarbital, pethidine, phenadoxone, phenomorphan, phenoperidine, piminodine, pholcodine, phenmetrazine, phenobarbital, phentermine, pinazepam, pipradrol, piritramide, prazepam, profadol, proheptazine, promedol, properidine, propoxyphene, remifentanil, secbutabarbital, secobarbital, temazepam, tetrazepam, triazolam, vinylbital, and zolpidem, or a pharmacologically acceptable salt, ester or solvate thereof.

5. The pharmaceutical composition of claim 1, further comprising an effective amount of an analgesic.

6. The pharmaceutical composition of claim 5, wherein the analgesic is acetaminophen.

7. The pharmaceutical composition of claim 1, wherein the organic vehicle is selected from the group consisting of caprylic acid, capric acid, oleic acid, palmitic acid, glyceryl monooleate, glyceryl monocaprylate, glyceryl monocaprate, glyceryl caprylate, caprate, propylene glycol monocaprate, propylene glycol monocaprylate, propylene glycol monolaurate, propylene glycol dilaurate, polyethylene glycol (PEG)-4 glyceryl caprylate, caprate, PEG-6 glyeryl linoleate, PGE-6 glyceryl linoleate, PEG-6 glyceryl oleate, caprylic/capric triglyceride, propylene glycol dicaprylate/dicaprate, soyabean oil and mixtures of two or more thereof.

8. The pharmaceutical composition of claim 1, wherein the co-solvent is a liquid ester.

9. The pharmaceutical composition of claim 8, wherein the co-solvent is selected from the group consisting of triethyl citrate, propylene glycol, a polyethylene glycol, triacetin, diethylene glycol monoethyl ether, and mixtures of two or more thereof.

10. The pharmaceutical composition of claim 1, wherein the co-solvent is present in an amount of about 10% to about 50%, by weight, based on the total weight of the composition.

11. The pharmaceutical composition of claim 1, wherein the organic vehicle is glyceryl caprylate/caprate, soyabean oil, olive oil, oleic acid, Caprylic/Capric Triglyceride, fish oil, propylene glycol monocaprylate, or a combination of two or more thereof.

12. The pharmaceutical composition of claim 11, wherein the co-solvent is propylene glycol, triethyl citrate, PEG-400 or a combination of two or more thereof.

13. The pharmaceutical composition of claim 1, further comprises a buffering agent.

14. The pharmaceutical composition of claim 1, further comprising an antioxidant.

15. The pharmaceutical composition of claim 14, wherein the antioxidant is selected from the group consisting of alpha-tocopherol, butylated hydroxytoluene, butylated hydroxyanisole, propyl gallate, and combinations of two or more thereof.

16. The pharmaceutical composition of claim 1, further comprising a viscosity-building agent selected from the group consisting of colloidal silicon dioxide, fumed silica, mesoporous silica and combinations of two or more thereof.

17. The pharmaceutical composition of claim 1, further comprising an opioid receptor antagonist selected from the group consisting of naloxone, naltrexone and methyl naltrexone.

18. The pharmaceutical composition of claim 1, wherein the pharmaceutically active agent is pre-treated with silica.

19. A method of rendering abuse resistant a pharmaceutically active agent susceptible to abuse, comprising preparing an immediate-release liquid pharmaceutical composition by mixing an effective amount of the pharmaceutically active agent, an organic vehicle, a surfactant, a co-solvent, and a viscosity-building polymer;
   wherein the organic vehicle, surfactant, and co-solvent co-elute with the pharmaceutically active agent when exposed to a solvent,
   wherein the organic vehicle is a C6-C18 fatty acid, a C6-C18 fatty acid mono-, di- or tri-glyceride, a C6-C18 fatty acid propylene glycol mono- or di-ester, a C6-C18 fatty acid polyethylene glycol ester, a vegetable oil, or a mixture of two or more thereof, and is present in an amount of about 50% to about 90% by weight, based on the total weight of the composition;
   wherein the surfactant is dioctyl sodium sulfosuccinate, sodium lauryl sulfate, PEG-32 glyceryl laurate, PEG-32 glyceryl palmitostearate, PEG-35 castor oil, PEG-8 glyceryl caprylate/caprate, PEG-6 glyceryl caprylate/caprate, PEG-40 hydrogenated castor oil, Macrogol 15 hydroxystearate, an ethylene oxide/propylene oxide block copolymer, polyoxyethylene 20 sorbitan monolaurate, polyoxyethylene 20 sorbitan monooleate, sorbitan monolaurate, sorbitan monooleate, tocopherol PEG succinate, polyoxyl 40 stearate, or a mixture of two or more thereof, and is present in an amount of about 2% to about 40%, by weight, based on the total weight of the composition;
   wherein the viscosity-building polymer is PEG-2M, PEG-5M, PEG-7M, PEG-14M, PEG-23M, PEG-45M, PEG-90M, or a combination of two or more thereof, and is present in an amount of about 0.5% to about 20% by weight, based on the total weight of the composition, so that it does not slow an immediate release of the pharmaceutically active agent from a single unit-dose administration, but slows the immediate release of the pharmaceutically active agent from a multiple unit-dose administration.

20. A method of deterring abuse of a pharmaceutically active agent susceptible to abuse, comprising administering the pharmaceutically active agent to a subject in need thereof, wherein the pharmaceutically active agent is formulated in a liquid pharmaceutical composition that comprises a mixture of an immediate release unit of a mixture of an effective amount of the pharmaceutically active agent, an organic vehicle, a surfactant, a co-solvent, and a viscosity-building polymer;
   wherein the organic vehicle, surfactant, and co-solvent co-elute with the pharmaceutically active agent when exposed to a solvent, wherein the organic vehicle is a C6-C18 fatty acid, a C6-C18 fatty acid mono-, di- or tri-glyceride, a C6-C18 fatty acid propylene glycol mono- or di-ester, a C6-C18 fatty acid polyethylene glycol ester, a vegetable oil, or a mixture of two or more thereof, and is present in an amount of about 50% to about 90% by weight, based on the total weight of the composition;

wherein the surfactant is dioctyl sodium sulfosuccinate, sodium lauryl sulfate, PEG-32 glyceryl laurate, PEG-32 glyceryl palmitostearate, PEG-35 castor oil, PEG-8 glyceryl caprylate/caprate, PEG-6 glyceryl caprylate/caprate, PEG-40 hydrogenated castor oil, Macrogol 15 hydroxystearate, an ethylene oxide/propylene oxide block copolymer, polyoxyethylene 20 sorbitan monolaurate, polyoxyethylene 20 sorbitan monooleate, sorbitan monolaurate, sorbitan monooleate, tocopherol PEG succinate, polyoxyl 40 stearate, or a mixture of two or more thereof, and is present in an amount of about 2% to about 40%, by weight, based on the total weight of the composition;

wherein the viscosity-building polymer is PEG-2M, PEG-5M, PEG-7M, PEG-14M, PEG-23M, PEG-45M, PEG-90M, or a combination of two or more thereof, and is present in an amount of about 0.5% to about 20% by weight, based on the total weight of the composition, so that it does not slow an immediate release of the pharmaceutically active agent from a single unit-dose administration, but slows the immediate release of the pharmaceutically active agent from a multiple unit-dose administration.

* * * * *